United States Patent [19]

Rollband

[11] Patent Number: 4,981,133
[45] Date of Patent: Jan. 1, 1991

[54] PRESSURE BANDAGE FOR PUNCTURE WOUNDS WITH A TARGET MARKETING

[76] Inventor: Ernest J. Rollband, 3415 Slaterville Rd., Brooktondale, N.Y. 14817

[21] Appl. No.: 419,160

[22] Filed: Oct. 10, 1989

[51] Int. Cl.$^5$ .................. A61F 13/00; A61F 15/00
[52] U.S. Cl. .................. 128/155; 128/157; 128/888
[58] Field of Search .............. 128/155, 157, 165, 888; 604/304, 307; 2/22, 24

[56] References Cited

U.S. PATENT DOCUMENTS

| | | |
|---|---|---|
| Re. 29,319 | 7/1977 | Nordby et al. |
| 2,221,758 | 11/1940 | Elmquist . |
| 2,340,142 | 1/1944 | Rauner . |
| 2,489,675 | 11/1949 | Roberts . |
| 2,579,403 | 12/1951 | Slomowitz et al. . |
| 3,026,874 | 3/1962 | Stevens . |
| 3,141,459 | 7/1964 | Orcutt .................. 128/157 |
| 3,297,032 | 1/1967 | Antonik . |
| 3,425,412 | 2/1969 | Pope . |
| 3,538,912 | 11/1970 | Becker . |
| 3,585,639 | 6/1971 | Enicks .................. 2/22 |
| 3,949,742 | 4/1976 | Nowakowski . |
| 4,202,331 | 5/1980 | Yale . |
| 4,399,816 | 8/1983 | Spangler . |
| 4,601,286 | 7/1986 | Kaufman . |
| 4,786,282 | 11/1988 | Wagle et al. .................. 604/307 |

FOREIGN PATENT DOCUMENTS 2840414  3/1980  Fed. Rep. of Germany ...... 128/888

Primary Examiner—Randall L. Green
Assistant Examiner—Paul Prebilic
Attorney, Agent, or Firm—Ralph R. Barnard

[57] ABSTRACT

A pressure bandage and method for using it is disclosed. The bandage comprises a piece of multi-layered absorbant material having a target marking on a bottom side and a corresponding target marking on a top side, wherein the target markings form a line which is substantially perpendicular to the plane of the bandage. The target marking on the bottom side of the bandage is aligned with the wound site and pressure is applied on the corresponding target marking on the top side of the bandage, thus permitting the application of pressure directly on the wound site.

10 Claims, 1 Drawing Sheet

PRESSURE BANDAGE FOR PUNCTURE WOUNDS WITH A TARGET MARKETING

BACKGROUND OF THE INVENTION

1. Field of the Invention

This invention relates to bandages, particularly to pressure bandages used to stop bleeding in puncture wounds. The large diameter needles used for kidney dialysis produce puncture wounds which require the application of pressure bandages.

2. Description of the Related Art

At present, when blood is drawn from a patient, the puncture wound which results is stopped by placing a piece of multi-layered gauze over the wound and applying pressure thereon. Until a clot forms and bleeding is substantially stopped, continual pressure must be exerted against the wound to prevent loss of blood. Because the gauze bandage which is placed on the wound is opaque, it is not possible to know the precise point at which to apply pressure. This is usually not a problem since under normal circumstances bleeding will stop in a matter of minutes as a clot forms over the wound.

In certain situations, however, a clot may take significantly longer to form. This can happen, for example, when a large needle is used, when an anticoagulant has been administered, or if the patient has poor clot-formation capabilities (e.g. if a patient is a hemophiliac).

This is a particular problem in kidney dialysis, since a large needle is used and an anticoagulant is often administered. In some cases, pressure must be continually applied for as long as half an hour before a clot is sufficiently formed to stop most of the bleeding. In such a situation, it is important to apply pressure directly over the wound site in order to minimize blood loss over time.

SUMMARY OF THE INVENTION

The pressure bandage of this invention comprises a piece of multi-layered absorbant material having a target marking on a bottom side and a corresponding target marking on a top side, such that the two target markings form a line which is substantially perpendicular to the plane of the bandage. These target markings allow the person applying the bandage to place pressure on the bandage at the site of the puncture wound.

In addition, if stitching is used to mark the target area on the pressure bandages of this invention, the multiple layers of absorbant material will hold together rather than flopping around. This makes it easier to hold the bandage in place.

The pressure bandage of this invention may also be used with a clamping means to apply pressure to the wound site. In this case, the patient would not have to apply manual pressure to the bandage. This is particularly helpful where the patient is physically incapable of exerting and/or maintaining enough pressure against the bandage.

Further objectives may be found in the following drawing, specification and claims.

DETAILED DESCRIPTION OF THE INVENTION

Figure 1:
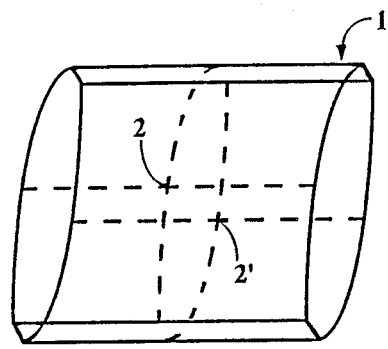
FIG. 1 is a plan view of the pressure bandage of the invention.

Referring now to the drawing in detail, FIG. 1 shows a pressure bandage (1) which has target markings (2, 2') in the form of stitched cross hairs. The bandage itself can be made from multiple layers of gauze or other absorbent material and the layers do not all have to be composed of the same type of material. For instance, the bandage could be made of a layer of gauze at the top, some thickness of cotton in the middle and another layer of gauze at the bottom. Thus, depending on the thickness and/or the absorbancy of the bandage material, the bandage can be made more or less absorbant.

The stitching shown in FIG. 1 is loose so as not to deform the bandage, but is secure enough to hold the layers of the bandage together. Although there are many other ways to mark the bandage, having cross hairs to mark the target area permits easier alignment of the bandage with the wound.

Figure 2:
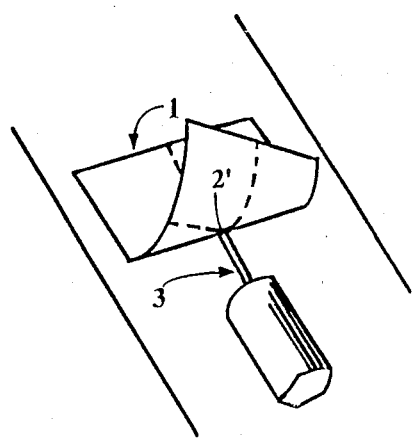
FIG. 2 shows the pressure bandage of the invention being placed on a wound.

FIG. 2 illustrates how to use such a bandage. Using the cross hairs on the bottom side of the bandage (2') as guides, the line of the needle (3) is aligned with the line of one of the stitches such that the line of the other stitch crosses the line of the first stitch at the wound site. A finger is then placed on the top side of the bandage at the point where the two cross hairs intersect and pressure is applied after the needle is withdrawn (not illustrated).

In another embodiment of the invention, the bandage (1) is placed on the wound site as described above, a piece of rigid material (5) is placed over the bandage and pressure is applied to the piece of rigid material rather than on the bandage itself. This permits the use of more than one finger at a time, resulting in an increase in overall pressure applied.

Figure 3:
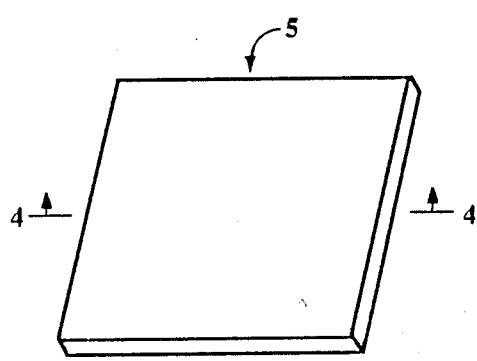
FIG. 3 is a plan view of a piece of rigid material used to provide additional pressure to a wound.

The rigid material can be a piece of wood, plastic, metal or any other such material which will withstand the application of finger pressure. The piece of rigid material must have at least one substantially flat surface which can be placed over the bandage. FIG. 3 is an example of a piece of rigid material which has two substantially flat surfaces. Although illustration shows a substantially rectangular piece, a number of other shapes would also permit the performance of the function described herein. If the piece of rigid material is clear, it will also be possible to observe the state of the bandage to determine if a fresh bandage must be applied.

Figure 4:
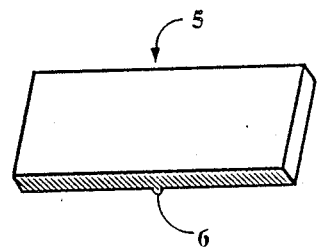
FIG. 4 is a cut side view of FIG. 3, taken substantially along the line 4—4. The piece of rigid material shown here includes a protrusion or dimple to concentrate the pressure exerted on a wound.

The location of a small protrusion or "dimple" (6) in the middle of said substantially flat surface of the piece of rigid material may provide a method of concentrating pressure on the wound site (see FIG. 4). By placing the piece of rigid material over the bandage so that the protrusion rests at the target marking on the top side of the bandage and applying pressure to said piece of rigid material, pressure is concentrated at the protrusion, and therefore, at the wound site.

A third embodiment of the invention further comprises a mechanical clamp means to apply pressure. It is directed to those situations where the patient cannot exert or maintain enough pressure on the bandage, even with the aid of a piece of rigid material as described above. This is achieved in the present invention by the use of a clamp means to apply pressure to the wound site.

Figure 5:
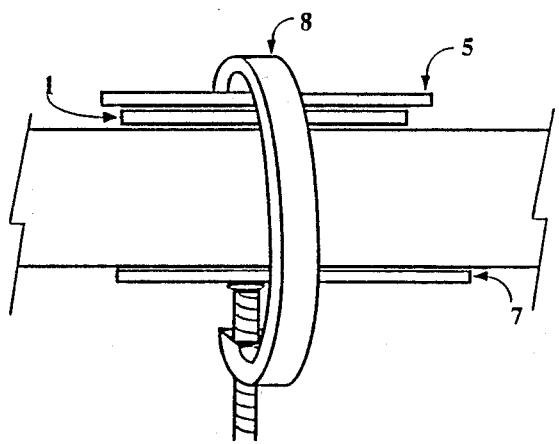
FIG. 5 is an exploded side view of the pressure bandage of the invention being used with a clamp means.

FIG. 5 illustrates a method of this invention utilizing a clamp means on a wound located on an arm or leg. The bandage is placed over the wound site and a first piece of rigid material (5) placed on top of the bandage (1) as described above. A second piece of rigid material (7), not necessarily composed of the same material as the first piece of rigid material, is placed on the far side of the arm or leg, opposite from the wound. A clamp (8) is then placed on the two pieces of rigid material and tightened so that pressure will be exerted against each of the two pieces of rigid material such that the two forces are of equal magnitude and opposite direction.

The foregoing description has been directed to particular embodiments of the invention in accordance with the requirements of the Patent Statutes for the purposes of illustration and explanation. It will be apparent, however, to those skilled in this art that many modifications and changes will be possible without departure from the scope and spirit of the invention. It is intended that the following claims be interpreted to embrace all such modifications.

What is claimed is:

1. A pressure bandage comprising a piece of multi-layered absorbant material having a bottom side and a top side, said bottom side having a bottom target marking indicating a bottom point which is a point on said bottom side and said top side having a top target marking indicating a top point which is a point on said top side, such that a straight line drawn through said bandage intersecting said top point and said bottom point is perpendicular to said top and bottom sides of said bandage.

2. The pressure bandage of claim 1 wherein said absorbant material is gauze.

3. The pressure bandage of claim 2 wherein each of said target markings comprises a set of cross hairs which can be used for alignment with the wound.

4. The pressure bandage of claim 1 wherein said absorbant material comprises multiple layers of cotton encased by at least one layer of gauze on said top and bottom sides.

5. Method of applying pressure to a wound, comprising the steps of:
   (a) selecting a bandage comprising a piece of multi-layered absorbant material having a bottom side and a top side, said bottom side having a bottom target marking indicating a bottom point which is a point on said bottom side and said top side having a top target marking indicating a top point which is a point on said top side, such that a straight line drawn through said bandage intersecting said top point and said bottom point is perpendicular to said top and bottom sides of said bandage,
   (b) placing said bandage on a puncture wound, said bottom point of said bandage being placed over the would site,
   (c) applying pressure at said top point of said bandage.

6. The method of claim 5 further comprising the steps of:
   (a) selecting a piece of rigid material having at least one substantially flat surface,
   (b) placing said piece of rigid material over said bandage, wherein said substantially flat surface is placed against said top side of said bandage,
   (c) applying pressure on said piece of rigid material at said top point of said bandage.

7. The method of claim 6 wherein said piece of rigid material is clear and allows observation of the underlying bandage.

8. Method of applying pressure to a wound on a body part, comprising the steps of:
   (a) selecting a bandage comprising a piece of multi-layered absorbant material having a bottom side and a top side, said bottom side having a bottom target marking indicating a bottom point which is a point on said bottom side and said top side having a top target marking indicating a top point which is a point on said top side, such that a straight line drawn through said bandage intersecting said top point and said bottom point is perpendicular to said top and bottom sides of said bandage,
   (b) placing said bandage on the wound, said bottom point being placed over the wound,
   (c) selecting a first piece of rigid material having at least one substantially flat surface,
   (d) placing said first piece of rigid material over said bandage, wherein said substantially flat surface is placed against said top side of said bandage,
   (e) applying pressure on said first piece of rigid material at said top point with a force vector substantially perpendicular to the substantially flat surface of said first piece of rigid material and wherein said pressure is being applied against the wound,
   (f) placing a second piece of rigid material in a position on the opposite side of said body part from said bandage and substantially parallel to said first piece of rigid material,
   (g) applying pressure to said second piece of rigid material, the pressure being applied to said second piece of material being equal and opposite to the pressure being applied to said first piece of rigid material,
   (h) using clamp means to apply said pressure to said first and second pieces of rigid material.

9. A method of making a pressure bandage comprising the steps of:
   (a) selecting a piece of multi-layered absorbant material
   (b) marking a target on a bottom side and a corresponding target on a top side, said bottom target marking indicating a bottom point which is a point on the bottom side of said bandage and said top target marking indicating a top point which is a point on the top side of said bandage, such that a straight line drawn through said bandage intersecting said top point and said bottom point is perpendicular to the top and bottom sides of said bandage.

10. The method of claim 9 comprising the further steps of indicating said top and bottom points by sets of cross hairs which can be used for alignment with a wound.

* * * * *